(12) United States Patent
Skiba et al.

(10) Patent No.: US 10,273,440 B2
(45) Date of Patent: Apr. 30, 2019

(54) DEVICES AND METHODS FOR CREATING AND TESTING MICROBES AND BIOFILMS

(71) Applicants: Jeffry B. Skiba, Chandler, AZ (US); Mina Izadjoo, Rockville, MD (US); Hosan Kim, Clarksville, MD (US)

(72) Inventors: Jeffry B. Skiba, Chandler, AZ (US); Mina Izadjoo, Rockville, MD (US); Hosan Kim, Clarksville, MD (US)

(*) Notice: Subject to any disclaimer, the term of this patent is extended or adjusted under 35 U.S.C. 154(b) by 0 days.

(21) Appl. No.: 14/933,085

(22) Filed: Nov. 5, 2015

(65) Prior Publication Data

US 2016/0122697 A1    May 5, 2016

Related U.S. Application Data

(60) Provisional application No. 62/075,343, filed on Nov. 5, 2014.

(51) Int. Cl.
| | |
|---|---|
| *C12M 3/00* | (2006.01) |
| *C12M 1/00* | (2006.01) |
| *C12M 1/12* | (2006.01) |
| *C12M 1/22* | (2006.01) |

(52) U.S. Cl.
CPC ............ *C12M 23/04* (2013.01); *C12M 23/10* (2013.01); *C12M 23/38* (2013.01); *C12M 25/14* (2013.01); *C12M 37/04* (2013.01)

(58) Field of Classification Search
CPC ....... C12M 21/00; C12M 23/10; C12M 41/14
See application file for complete search history.

(56) References Cited

U.S. PATENT DOCUMENTS

| | | | | | |
|---|---|---|---|---|---|
| 4,294,931 | A | * | 10/1981 | Levin et al. ............. | C12Q 1/16 206/362 |
| 2011/0077348 | A1 | * | 3/2011 | Erdem ................. | C08G 18/283 524/539 |

OTHER PUBLICATIONS

Wright et al., "Inexpensive low-oxygen incubators", Nature Protocols, vol. 1 No. 4 2006, p. 2088-2090 (Year: 2006).*
Fluorolab, "FEP Petri Dish Liners", https://fluorolab.com/product/fep-petri-dish-liners/ (Year: 2018).*

* cited by examiner

Primary Examiner — Ruth A Davis
(74) Attorney, Agent, or Firm — Hayes Soloway PC

(57) ABSTRACT

Systems and methods for growing microbes and biofilms on a hydrogel in a controlled environment. The system can have a cup, and a liner with the liner inserted into the cup and a hydrogel inserted into the liner. The cup, liner, and hydrogel assembly can be placed into a containment tray. The hydrogel can be sterilized before being placed into the containment tray. A lid can seal the cup, liner, and hydrogel into the containment tray. A lid can have inoculations ports, or can be made out of a self-sealable material keeping the inside environment sterilized and free of contaminants. The hydrogel can be inoculated with microbes through the inoculations ports, and incubated for a period of time at a set temperature to allow the microbes, and biofilms time to grow. After being grown the microbes and biofilms can be separated from each other allowing for both microbes and biofilm to be separately tested.

10 Claims, 4 Drawing Sheets

DEVICES AND METHODS FOR CREATING
AND TESTING MICROBES AND BIOFILMS

CROSS-REFERENCE TO RELATED APPLICATION

This application claims the benefit of U.S. Provisional Application No. 62/015,343, filed Nov. 5, 2014.

FIELD OF THE INVENTION

The present specification relates to systems and methods for creating biofilms in a controlled environment, more specifically systems and methods for creating microbes and biofilms, which can allow for a biofilm system to produce a more uniform and reproducible test samples.

BACKGROUND OF THE INVENTION

According to the National Institutes of Health, organisms in a biofilm state cause 80% of all infectious diseases. Biofilms are the predominant cause of chronic pulmonary infections in Cystic Fibrosis, Ventilator Associated Pneumonia, burn infections, and wound infections. Biofilm infections are up to a thousand times more difficult to treat than conventional infections.

Biofilms are the result of single or multi-colony bacteria living together in a group. When the group has sufficient population, a protective film is formed over the colony. Biofilms can be responsible for inter and intra bacterial communication as well as modifying the genetic expression within the colony. Biofilms can be present in almost all environments, such as water supply systems, oil wells and pipes, and human tissues.

Biofilms are a very important part of the natural environment and can be beneficial. However, biofilms can profoundly affect human health and industrial productivity. Biofilms pervasiveness effects human health, water quality, corrosion, and power generation efficiency. Additionally, biofilms contaminate surfaces in the food processing industry, and deteriorate air quality in ventilation and air handling systems. Biofilms infections and related complications cost the United States billions of dollars per year.

Clinical wound pathogens associated with chronic infections are often associated with the formation of single or polymicrobial biofilms leading to impaired wound healing and clinical complications. In order to effectively test bacteria in biofilms, they must be grown in an appropriate laboratory environment with proper controls to assure integrity of the sample. Currently, there is no technologies or systems that can effectively grow biofilms quickly with uniformity and reproducibility. A system and method is needed in the industry that can quickly and efficiently grow microbes and biofilms, and can generate robust and efficient in-vitro testing of anti-biofilm properties for wound care products, oil field biofilm prevention, water system biofilm prevention and others.

SUMMARY

The present specification is directed to systems and methods for creating or growing microbes and biofilms in a hydrogel in an environment that can be controlled producing uniformity and reproducibility within sample populations for testing purposes Aspects disclosed herein include systems and methods of growing and testing microbes and biofilms. In one embodiment, a system comprises a liner inserted into a cup, which can be substantially support by the cup. In addition, a microbe and biofilm growing system can comprise a hydrogel that can be inserted into the liner, cup assembly. In embodiments, a hydrogel, liner, cup assembly can be placed into a containment tray where the environment within the containment tray such as, for example, the temperature, pressure, humidity, or the like can be controlled. A lid can be placed over the containment tray creating an environment within the containment tray that free of contaminants. The hydrogel can be inoculated through a self-sealing lid or one or more ports in the lid or containment tray. In certain embodiments a lid can have either a slot with a membrane-like filter (e.g., 0.45 µm, or finest one), or the lid can be the membrane-like filter allowing for aerobic and anaerobic bacterial respiration.

A single microbial and biofilm containment system, or multiple microbial and biofilm containment systems can be connected for either a single sample, or a plurality of samples, such as, for example, one sample, two samples, one control sample, two control samples, or multiple samples and multiple control samples. In general, a microbe and biofilm system can hold one or more containment systems, which can be customizable to the users specifications.

In embodiments a method of growing and testing microbial biofilms can create a containment system that can be sterilized. A hydrogel can be placed inside a containment device, which can be sealed with either a breathable or impermeable lid. A containment system, and hydrogel can be sterilized. The hydrogel can be inoculated through a self-sealing lid or a self-sealing port on the lid. A containment system, inoculated hydrogel can be incubated at a user's specific environment controlling the temperature, pressure, and/or humidity within the containment system.

Additional features and advantages of the present invention will become apparent to those skilled in the art upon consideration of the following detailed description.

BRIEF DESCRIPTION OF THE DRAWINGS

These and other features, aspects, and advantages of the present specification will become better understood with regard to the following description, appended claims, and accompanying drawings where:

DETAILED DESCRIPTION

The embodiments of the invention described herein are not intended to be exhaustive or to limit the invention to precise forms disclosed. Rather, the embodiments selected for description have been chosen to enable one skilled in the art to practice the invention.

The present specification relates to systems and methods for creating or growing, and testing microbes, and biofilms.

"Containment System" as used herein can be any combination of parts such as, for example, a lid, a containment tray, a cup, a hydrogel, a support body, and a liner, which can be used as one system, two systems, three systems, or the like that can create a controllable environment.

"Containment Environment" as used herein can be can be the space within the lid and containment tray where microbes, and biofilm can grow or be created.

"Hydrogels" as used herein can be any type of hydrogel, such as but not limited to poloxamer, dextran, chitosan, collagen, dextran sulfate, PEG-PLA-PEG, poly vinyl alcohol, any polymer based materials, or any mix of the materials.

"Inoculation" as used herein refers to adding a known amount of the desired bacterial or fungal or other potential biofilm-making microorganisms using a syringe needle or other method of inoculation.

"Liner" as used herein can be glass, plastic, metal, PTFE, polymer, or any type of material that can be act as a barrier between a cup, and a hydrogel.

"Microbes" as used herein refers to bacteria, single cell organisms, viruses, fungi, protozoa, or the like.

"Polymers" as used herein refers to carboxlic acid groups, such as, for example, sodium polyacrylate, or it can be synthetic, or natural/synthetic hybrid polymers.

"Support Body" as used herein refers to a body that can support a containment tray, lid, cup, liner, and hydrogel assembly, which can be one or more support bodies.

Systems for Creating Microbes, and Biofilms

Figure 1:
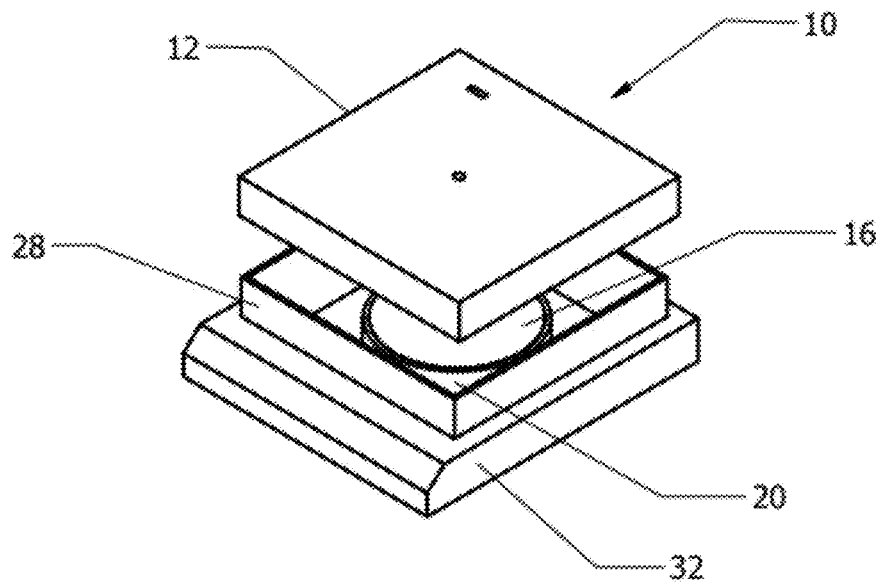
FIG. 1 is an orthogonal view of the containment system for creating microbes, and biofilms.
Figure 2:
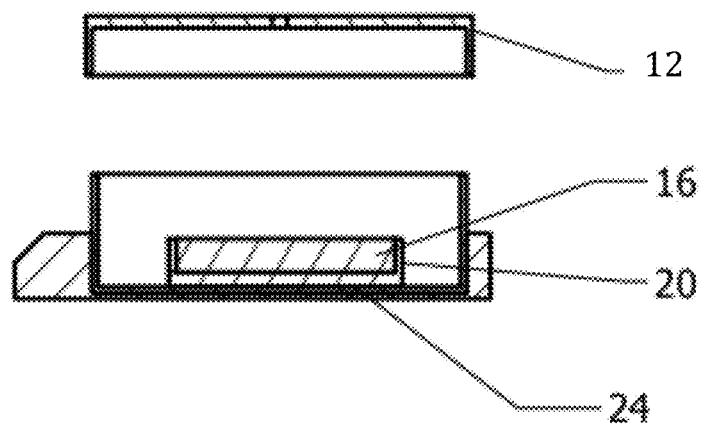
FIG. 2 is a cross-sectional view of the containment system for creating microbes, and biofilms.

Referring initially to FIG. 1, and FIG. 2, a system for creating or growing microbes, and biofilms is shown generally at 10. Embodiments comprise a liner 24 which can be inserted into a cup 20. A liner 24 can take on the form of a cup 20 having a bottom and plurality of sides, or a liner can be a slide placed on the bottom of a cup having a bottom and a top. A cup 20 can be circular, square, rectangular, or the like in shape having a bottom and sides. In embodiments a hydrogel 16 can be placed into a liner 24 and cup 20 assembly, and taking the shape of the cup, liner assembly, or it can take on its own form or shape. In certain embodiments a hydrogel 16 can be a liquid, solid, gel or the like. In embodiments a liner 24 can allow for a hydrogel to be easily removed from a cup 20. In certain embodiments a liner 24, cup 20, and hydrogel 16 can vary in size to accommodate larger or smaller quantities of microbes, and biofilms to be grown.

In embodiments a cup 20, liner 24, and hydrogel 16 can be place into a containment tray 28. In embodiments a containment tray 28 can be such as, for example, a circular, a square, a rectangular, or the like in shape, having a bottom and plurality of sides forming an area in which an environment within the area can be controlled. In certain embodiments a containment tray 28 can vary in size to accommodate various sized cups 20, liner 24, and hydrogel 16 assembly. In embodiments a lid 12 can be place onto or sealed against a containment tray 28, which can cover, protect, and insulate a hydrogel 16, a liner 24, and a cup 20 from outside elements, such as air, and other contaminants. In embodiments a lid 12 can be such as, for example, a circular, a square, a rectangular, or the like in shape, having a bottom and sides. In other embodiments a lid can be flat having a top and bottom, and having a surface that is sealable against a containment tray 28 such as, for example, a lid can be screwed on, sealed to, place on, or the like to a containment tray. In certain embodiments a lid 12 can have a slot 14 for ventilation that allows air or gases to exit and/or enter the inside environment that can be created by a containment tray and lid. In addition, in certain embodiments a lid can have a port or self-sealable hole 18 for inoculation. In certain embodiments a lid 12 can be permeable so that fluid or gases can pass through the lid, or a lid can be impermeable to not allow any fluid or gas to pass through and get to a hydrogel 16, cup 20, and liner 24 assembly. In certain embodiments a slot 14 for ventilation can be a hole that can be such as, for example, a square, circular, spherical, triangular, or the like.

In certain embodiments a slot 14 can be a breathable material, which can be attached to a lid 12 such as, for example, a membrane filter, a glass fiber filter, a cellulose filter paper, a quartz filter, or the like to allow gases or liquids to permeate either out of or in to a containment tray. In certain embodiments a lid 12 can have a port 18 for inoculation, which can be an open hole or the lid have a hole with a membrane, a self-sealable material attached to it, which can allow a needle or other tubes to penetrate through the lid to inoculate a hydrogel 16 keeping any contaminants from entering the enclosure that the lid and containment tray 28 create. In other embodiments a lid 12 can be such as, for example, a self-sealable material, a membrane, or the like that can allow inoculation without letting contaminants into a containment tray 28, lid 12 enclosure and controllable environment. In certain embodiments a containment tray 28, lid 12, cup 20, liner 24, hydrogel 16 assembly can be placed on a support body 32. In other embodiments a containment tray 28, lid 12, cup 20, liner 24, hydrogel 16 assembly can be used without a support body 32.

Figure 3:
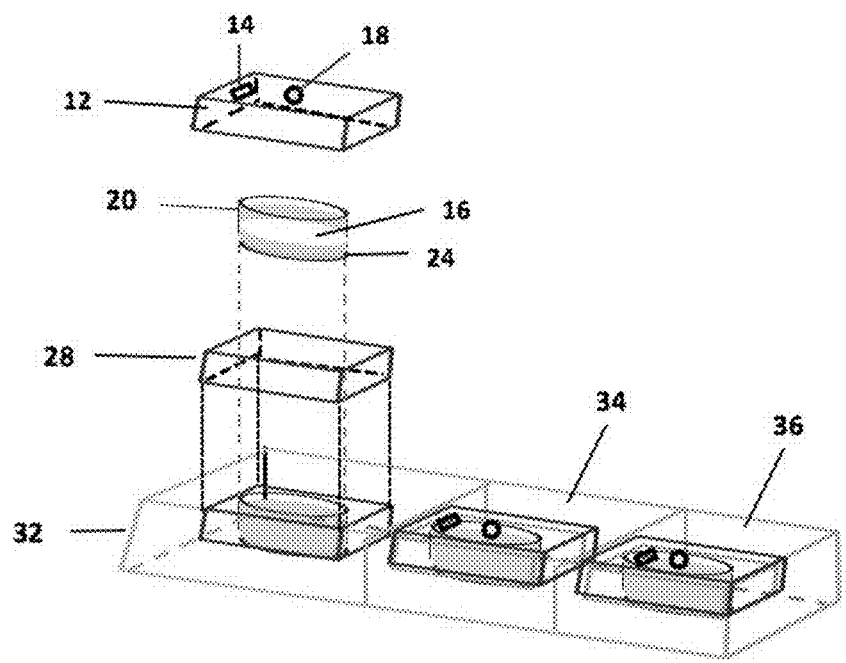
FIG. 3 illustrates a detailed view of an embodiment as disclosed herein.

As illustrated in FIG. 3, in embodiments a containment tray 28, lid 12, cup 20, liner 24, hydrogel 16 assembly can be more than one assembly such as for example, one assembly, two assemblies, three assemblies, four assemblies, five assemblies, six assemblies, seven assemblies, eight assemblies, or the like. In addition, in certain embodiments a containment tray can be made as one, two, three, four, five, six, seven, or the like containment trays, or it can be made as one containment tray that can be connected to one or multiple other containment trays. In certain embodiments a support body 32 can be included in a containment tray 28, lid 12, cup 20, liner 24, hydrogel 16 assembly. A support body 32 can be made as one, two, three, four, five, six, seven, or the like support bodies, or it can be made as one support body that can be connected to plurality of other support bodies.

Methods of Creating Microbes and Biofilms

Figure 4:
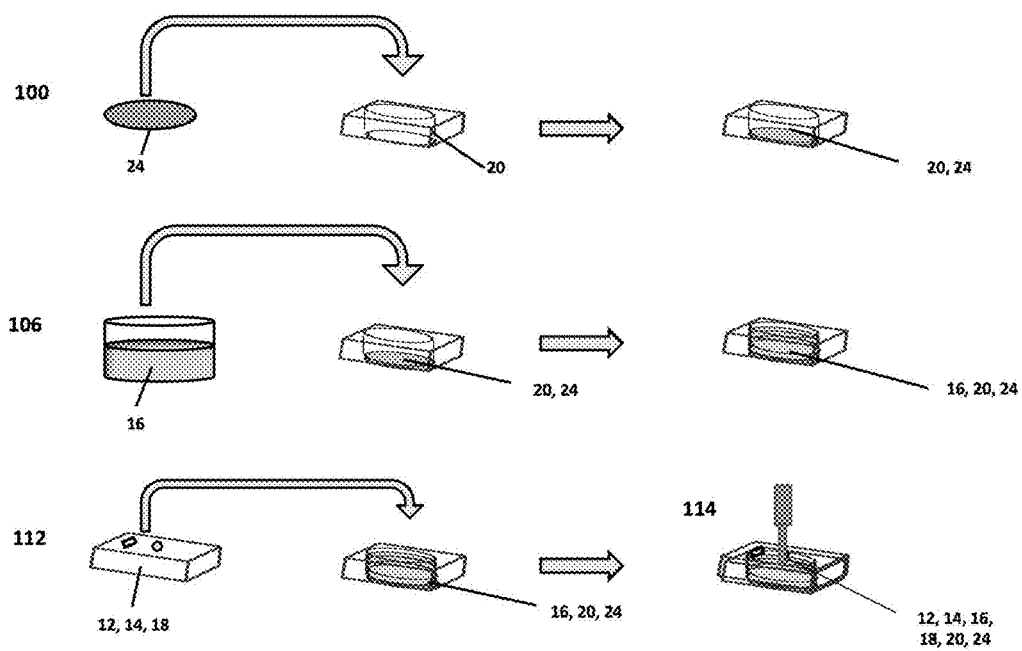
FIG. 4 illustrates steps within a method for creating microbes and biofilms.
Figure 5:
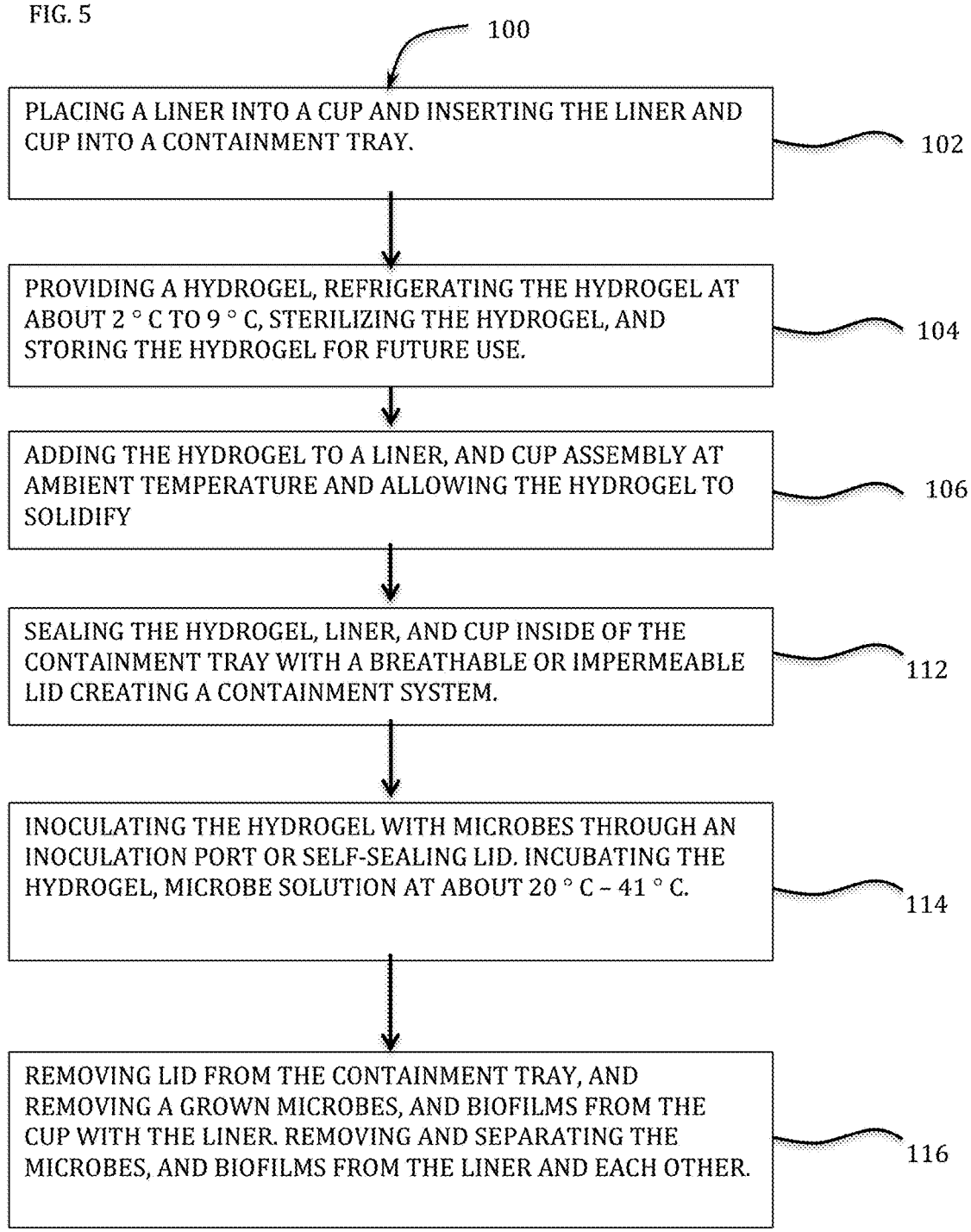
FIG. 5 shows a method for growing microbes and biofilms in a controlled environment.

With reference to FIG. 4, and FIG. 5 an illustrative method 100 of growing microbes and biofilms includes placing a liner 24 into a cup 20 and inserting the liner and cup into a containment tray 28 at step 100. A liner 24 can allow for easy removal of the biofilm from the cup 20. In certain embodiments a liner 24 can be omitted and a hydrogel 16 can be placed directly into a cup 20.

In preparation to step 106, at step 104 a hydrogel 16 can be created from a polymer or premade hydrogels can be used. A polymer can be incorporated into a desired microorganism growth medium at a user specified concentration, which can be added slowly on a ice bath and can be stirred into the growth medium, and can be dissolved completely. In embodiments the microorganism growth medium can be either custom manufactured or a commercial microorganism growth medium such as, for example, Mueller-Hinton broth, Tryptic Soy broth, or the like. In embodiments the user specified concentration can be less than 1% (w/v), less than 2% (w/v), less than 3% (w/v), less than 4% (w/v), less than 5% (w/v), less than 6% (w/v), less than 7% (w/v), less than 8% (w/v), less than 9% (w/v), less than 10% (w/v), less than 15% (w/v), less than 20% (w/v), less than 25% (w/v), less than 30% (w/v), or the like. In embodiments a user specified concentration can be more than 1% (w/v), more than 2% (w/v), more than 3% (w/v), more than 4% (w/v), more than 5% (w/v), more than 6% (w/v), more than 7% (w/v), more than 8% (w/v), more than 9% (w/v), more than 10% (w/v), more than 15% (w/v), more than 20% (w/v), more than 25% (w/v), more than 30% (w/v), or the like.

In embodiments a hydrogel 16 can be refrigerated overnight at about 4° C. In certain embodiments the hydrogels can be refrigerated overnight at, at least 1° C., at least 2° C., at least 3° C., at least 4° C., at least 5° C., at least 6° C., at least 7° C., at least 8° C., at least 9° C., or the like. In certain embodiments hydrogels are refrigerated at most 1° C., at most 2° C., at most 3° C., at most 4° C., at most 5° C., at most 6° C., at most 7° C., at most 8° C., at most 9° C., or the like.

A hydrogel can be autoclaved at about 121° C. for about 15 minutes, or can be sterilized by other sterilization techniques, and can be stored at about 4° C. About 200 µl of about 30% hydrogel 16 can be inserted onto a liner 24, and cup 20. The amount of hydrogels applied can vary depending on the scale of biofilms generated or the characteristic of sample or specimen tested. In certain embodiments a hydrogel 16 can be autoclaved at least 110° C., at least 111° C., at least 112° C., at least 113° C., at least 114° C., at least 115° C., at least 116° C., at least 117° C., at least 118° C., at least 119° C., at least 120° C., at least 121° C., at least 122° C., at least 123° C., at least 124° C., at least 125° C., at least 126° C., or the like. In certain embodiment a hydrogel 16 can be autoclaved at most 110° C., at most 111° C., at most 112° C., at most 113° C., at most 114° C., at most 115° C., at most 116° C., at most 117° C., at most 118° C., at most 119° C., at most 120° C., at most 121° C., at most 122° C., at most 123° C., at most 124° C., at most 125° C., at most 126° C., or the like.

In embodiments a hydrogel 16 can be autoclaved for at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, or the like. In certain embodiments a hydrogel 16 can be autoclaved for at most 1 minute, at most 2 minutes, at most 3 minutes, at most 4 minutes, at most 5 minutes, at most 6 minutes, at most 7 minutes, at most 8 minutes, at most 9 minutes, at most 10 minutes, at most 11 minutes, at most 12 minutes, at most 13 minutes, at most 14 minutes, at most 15 minutes, at most 16 minutes, at most 17 minutes, or the like.

In certain embodiments a hydrogel 16 can be stored for future use at least 1° C., at least 2° C., at least 3° C., at least 4° C., at least 5° C., at least 6° C., at least 7° C., at least 8° C., at least 9° C., or the like. In certain embodiments hydrogel 16 can be stored at most 1° C., at most 2° C., at most 3° C., at most 4° C., at most 5° C., at most 6° C., at most 7° C., at most 8° C., at most 9° C., or the like.

Figure 6:
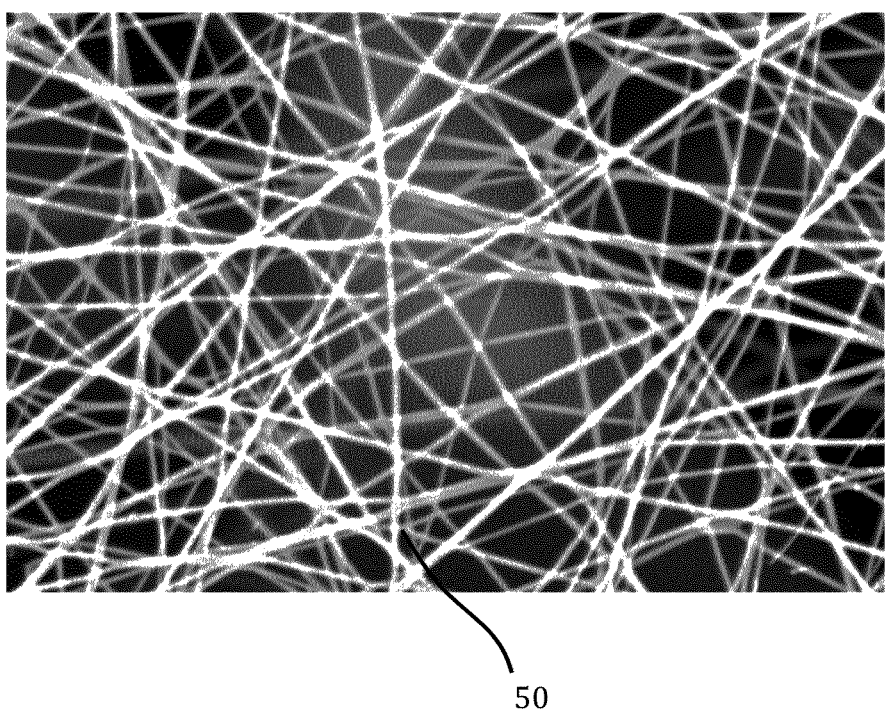
FIG. 6 shows a nano-sized hydrogel scaffold structure where microbes and biofilms can connect to each other and grow.

At step 106, a hydrogel 16 can be added into a liner 24 and cup 20, which can be inserted into a containment tray 28. A hydrogel 16 can be a network forming material that can have aggregating molecules, particles, or polymers that can form extended elongated structures that can interconnect or can form crosslinks 50, such as a scaffold structure, between each segment as shown in FIG. 6. A hydrogel 16 can be a suitable environment for microbes and biofilms to grow quickly between the interconnections and/or crosslinks within the elongated hydrogel's structures. The microbes can attached quickly to the hydrogel and change from a planktonic (free floating) microbe to a stationary microbe capable of being replicated and can begin expression of quorum sensing genes. As a result quorum sensing response is effected more rapidly from the microbes in the nutrient bas that can initiate the creation of biofilms. The hydrogel 16, cup 20, liner 24 assembly can be incubated at ambient temperature to allow the hydrogel to solidify. In embodiments a hydrogel 16 can be added to a liner 24, and cup 20 of at least 1%, at least 2%, at least 3%, at least 4%, at least 5%, at least 6%, at least 7%, at least 8%, at least 9%, at least 10%, at least 15%, at least 20%, at least 25%, at least 30%, or the like. In certain embodiments hydrogels are added on top of the cover slip of at most 1%, at most 2%, at most 3%, at most 4%, at most 5%, at most 6%, at most 7%, at most 8%, at most 9%, at most 10%, at most 15%, at most 20%, at most 25%, at most 35%, or the like. In embodiments a hydrogel 16 can be incubated for at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, or the like. In certain embodiments a hydrogel 16 can be incubated for at most 1 minute, at most 2 minutes, at most 3 minutes, at most 4 minutes, at most 5 minutes, at most 6 minutes, at most 7 minutes, at most 8 minutes, at most 9 minutes, at most 10 minutes, at most 11 minutes, at most 12 minutes, or the like.

In certain embodiments a 30% hydrogel 16 can be at least 195 µl, at least 196 µl, at least 197 µl, at least 198 µl, at least 199 µl, at least 200 µl, at least 201 µl, at least 201 µl, at least 202 µl, at least 203 µl, or the like. In certain embodiments a 30% hydrogel 16 can be at most 195 µl, at most 196 µl, at most 197 µl, at most 198 µl, at most 199 µl, at most 200 µl, at most 201 µl, at most 201 µl, at most 202 µl, at most 203 µl, or the like.

At step 112, a lid 12 can be attached, screwed, or sealed onto a containment tray 28 creating a suitable environment inside the lid and containment tray that can grow microbes, and create biofilms. A lid 12 can be a breathable or impermeable barrier between a hydrogel 16, cup 20, liner 24 assembly that can be sit inside of an environment that the lid and a containment tray 28 create. Depending upon a users desired microbial and biofilm growth rate an environment that can be created inside of a lid 12 and containment tray 28 can be aerobic, or anaerobic. In addition, a user can control the temperature, pressure, humidity, or the like within the environment created by a lid 12 and containment tray 28. A lid 112, hydrogel 16, cup 20, liner 24, and containment tray 28 assembly can be a single system or can be a plurality of systems. (See FIG. 3). In embodiments a lid 112, hydrogel 16, cup 20, liner 24, and containment tray 28 assembly can be sterilized to prevent any unwanted microbes from growing within the assembly.

At step 114, inoculating a hydrogel 16 with microbes through an inoculation port 18 or self-sealing lid. A microbe, hydrogel 16 solution can be incubated at about 35° C. In certain embodiments an incubation temperature can be at least 20° C., at least 21° C., at least 22° C., at least 23° C., at least 24° C., at least 25° C., at least 26° C., at least 27° C., at least 28° C., at least 29° C., at least 30° C., at least 31° C., at least 32° C., at least 33° C., at least 34° C., at least 35° C., at least 36° C., at least 37° C., at least 38° C., at least 39° C., at least 40° C., at least 41° C., or the like. In certain embodiments an incubation temperature can be at most 20° C., at most 21° C., at most 22° C., at most 23° C., at most 24° C., at most 25° C., at most 26° C., at most 27° C., at most 28° C., at most 29° C., at most 30° C., at most 31° C., at most 32° C., at most 33° C., at most 34° C., at most 35° C., at most 36° C., at most 37° C., at most 38° C., at most 39° C., at most 40° C., at most 41° C., or the like.

In embodiments an incubation temperature can be dependent on the appropriated temperature of a user's selected microorganisms or microbes being tested. An incubation period can be incubated in a laboratory setting or the biofilm system can be equipped with its own heating source for field setting and applications. In embodiments incubation temperatures can be achieved in a laboratory setting using environmental control chambers. In certain embodiments incubation temperatures can be controlled outside of a laboratory environment using battery powered heaters, or chemical heaters attached to either a support body 32, or containment tray 28 such as, for example, self-activating warmers, battery powered heating elements, water heating element, ceramic heating elements, composite heating elements, gas heating elements, or the like.

In embodiments a biofilm growth system can have one, two, three, four, five, six, seven, eight, or the like lid 112, hydrogel 16, cup 20, liner 24, and containment tray 28 assembly each with either the same type of desired biofilm and microbes, or each with different types of biofilms and microbes. In certain embodiments one, two, three, four, five, six, seven, eight or the like lid 112, hydrogel 16, cup 20, liner 24, and containment tray 28 assembly can be either a control such as, for example, distilled water, buffer, medium, or the like, or it can be a known microbe such as, for example, *e. coli, p. aeruginosa*, or the like. In embodiments lid 112, hydrogel 16, cup 20, liner 24, and containment tray 28 assembly can be stored at ambient temperature.

At step 116, a lid 20 can be removed from a containment tray 28, and the grown microbes, and biofilms can be removed from a cup 20 with or without a liner 24. To check the bacterial load affected by antimicrobials or other active ingredients, a liner 24 holding biofilms can be placed into a chilled tube or flask containing phosphate buffered saline, a buffer on ice, or the like. Microbes, and biofilms can be separated from a liner 24 by vortex and sonication with a type of sonicator, or ultrasonic water bath, and microorganisms/microbes can be released from the biofilms. Serials dilutions of the microbial suspensions can be made and plated onto bacterial agar plates. After appropriate incubation temperature and time, the number of surviving colonies can be determined and tested.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only and is not intended to limit the scope of the present disclosure, which is defined solely by the claims. Accordingly, embodiments of the present disclosure are not limited to those precisely as shown and described.

Certain embodiments are described herein, including the best mode known to the inventors for carrying out the methods and devices described herein. Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosed embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present disclosure and does not pose a limitation on the scope of the embodiments otherwise claimed. No language in the present specification should be construed as indicating any non-claimed element essential to the practice of the disclosed embodiments.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

What is claimed is:

1. A microbe and biofilm growing system comprising:
  a cup open at a top end and having a bottom section and a plurality of side sections;

a liner having a bottom section and a plurality side section wherein said liner is inserted into said cup;

a hydrogel placed on said liner and in said cup;

a containment tray having a bottom section and a plurality of side sections wherein said cup, said liner, and said hydrogel are placed into said containment tray;

a lid including a ventilating slot, and a self-sealable injection port, wherein said lid is adapted to cover said cup open top end, and to seal against said containment tray whereby to create an environment that is suitable for sterilization, and microbial and biofilm growth.

2. A microbe and biofilm growing system as set forth in claim 1, wherein said hydrogel is a growth media that provides a microstructure and nutrition for microbial and biofilm growth.

3. A microbe and biofilm growing system as set forth in claim 1, further comprising a support base.

4. A microbe and biofilm growing system as set forth in claim 3, wherein said support base is attached to said containment tray.

5. A microbe and biofilm growing system as set forth in claim 1, wherein said lid is permeable, or impermeable to surrounding elements.

6. A microbe and biofilm growing system as set forth in claim 1, wherein said lid is adapted to be screwed onto said containment tray.

7. A microbe and biofilm growing system as set forth in claim 1, wherein said lid is also adapted to seal to said containment tray.

8. A method of growing microbes and biofilms in a biofilm growing system as claimed in claim 1, comprising:

placing said liner into said cup, and inserting said liner, and said cup into said containment tray;

providing said hydrogel; cooling said hydrogel to about 2° C. to about 9° C.; sterilizing said hydrogel, and storing said hydrogel for future use;

adding said hydrogel to said liner, and said cup at ambient temperature, and allowing said hydrogel to solify;

sealing said containment tray with said hydrogel, said cup, and said liner inside with a lid;

inoculating said hydrogel with microbes;

incubating said hydrogel, and said microbe solution at about 20° C. to about 41° C.

removing said lid from said containment tray, and removing grown microbes, and biofilms from said cup with said liner; removing said grown microbes and biofilms from said liner; separating said microbes and said biofilms from each other.

9. A method of growing microbes and biofilms in a biofilm growing system as set forth in claim 1, wherein inoculation is done through a port in said lid or a self-sealing hole in said lid.

10. A method of growing microbes and biofilms in a biofilm growing system as set forth in claim 1, further comprising placing said liner, said cup, said hydrogel, said containment tray, and said lid onto a support base.

* * * * *